United States Patent
Kamihara et al.

(10) Patent No.: US 10,578,576 B2
(45) Date of Patent: Mar. 3, 2020

(54) JOINT EVALUATION METHOD

(71) Applicant: MITSUBISHI HEAVY INDUSTRIES, LTD., Tokyo (JP)

(72) Inventors: Nobuyuki Kamihara, Tokyo (JP); Toshio Abe, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 162 days.

(21) Appl. No.: 15/578,011

(22) PCT Filed: Sep. 1, 2016

(86) PCT No.: PCT/JP2016/075719
§ 371 (c)(1),
(2) Date: Nov. 29, 2017

(87) PCT Pub. No.: WO2017/073162
PCT Pub. Date: May 4, 2017

(65) Prior Publication Data
US 2018/0292344 A1 Oct. 11, 2018

(30) Foreign Application Priority Data
Oct. 28, 2015 (JP) .................................. 2015-211949

(51) Int. Cl.
*G01R 31/02* (2006.01)
*G01N 27/24* (2006.01)
*G01N 27/20* (2006.01)

(52) U.S. Cl.
CPC ........... *G01N 27/24* (2013.01); *G01N 27/205* (2013.01)

(58) Field of Classification Search
USPC ......... 324/71.1, 713, 715, 717, 718; 73/850, 73/851
See application file for complete search history.

(56) References Cited

U.S. PATENT DOCUMENTS 4,004,456 A * 1/1977 Vahaviolos ............ G01N 19/04
73/801
5,245,293 A 9/1993 Runner
(Continued)

FOREIGN PATENT DOCUMENTS

JP 51-129281 11/1976
JP 2-275349 11/1990
(Continued)

OTHER PUBLICATIONS

International Search Report dated Nov. 22, 2016 in International (PCT) Application No. PCT/JP2016/075719.
(Continued)

*Primary Examiner* — Vincent Q Nguyen
(74) *Attorney, Agent, or Firm* — Wenderoth, Lind & Ponack, L.L.P.

(57) ABSTRACT

A joint evaluation method of evaluating a joint state of a joint portion in a composite including the joint portion in which a first adherend and a second adherend are joined to each other through an adhesive is provided. The joint evaluation method includes applying an alternating-current signal to the joint portion; changing frequency to measure current and voltage; calculating an evaluation value related to a given electrical characteristic from a current value and a voltage value obtained by the measurement; comparing the evaluation value with a preset criterion related to the given electrical characteristic; and evaluating the joint state of the joint portion according to an amount of deviation of the evaluation value from the preset criterion.

6 Claims, 4 Drawing Sheets

(56) References Cited

U.S. PATENT DOCUMENTS

| | | | |
|---|---|---|---|
| 5,665,913 A | 9/1997 | Chung | |
| 5,764,859 A | 6/1998 | Kim et al. | |
| 5,841,031 A | 11/1998 | Chung | |
| 2005/0274455 A1* | 12/2005 | Extrand | C09J 5/00 156/272.4 |
| 2011/0089958 A1 | 4/2011 | Malecki et al. | |
| 2011/0187391 A1 | 8/2011 | Bach et al. | |

FOREIGN PATENT DOCUMENTS

| | | |
|---|---|---|
| JP | 3-60384 | 9/1991 |
| JP | 8-122286 | 5/1996 |
| JP | 9-89825 | 4/1997 |
| JP | 10-332619 | 12/1998 |
| JP | 11-77323 | 3/1999 |
| JP | 2008-142739 | 6/2008 |
| JP | 2013-508722 | 3/2013 |

OTHER PUBLICATIONS

Written Opinion of the International Searching Authority dated Nov. 22, 2016 in International (PCT) Application No. PCT/JP2016/075719.

Extended European Search Report dated Jun. 21, 2018 in corresponding European Patent Application No. 16859399.4.

Ryosuke Matsuzaki et al., "Wireless detection of internal delamination cracks in CFRP laminates using oscillating frequency changes", Composites Science and Technology, vol. 66, No. 3-4, pp. 407-416.

* cited by examiner

JOINT EVALUATION METHOD

BACKGROUND OF THE INVENTION

1. Field of the Invention

The present invention relates to a joint evaluation method.

2. Description of Related Art

In recent years, composites have been used as structure materials for structures, such as aircraft, automobiles, vehicles, and ships (see Japanese Translation of PCT International Application, Publication No. 2013-508722 (paragraph {0004})). A composite is a material composed of a resin material mixed with a reinforcing material, such as carbon fibers.

Some structures include a joint structure composed of structure materials joined to each other. Jointing uses fastener members, such as a bolt and a nut, an adhesive, or the like. To ensure reliability, a joint state in a product including a joint structure needs to be inspected. Inspection of joint state traditionally employs a non-destructive technique using ultrasound waves.

An adhesive provides a bond between adherends by the anchoring effect (a physical bond) or a chemical bond. When members of composites are bonded to each other with an adhesive, contaminations or the like on the surfaces may cause an extreme reduction in adhesion (joint strength). The state where an adhesive provides low chemical adhesion due to such contaminations or the like on the surfaces is referred to as kissing bond.

A kissing bond, which is not a reduction in physical adhesion caused by the presence of a gap or the like, cannot be detected by a non-destructive technique using ultrasound waves. A kissing bond can be detected by a technique using lasers but this technique inevitably destroys a bonding interface with lasers. Therefore, product inspection cannot be performed with a technique using lasers.

A method of evaluating a kissing bond with a non-destructive technique has currently not been established; thus, reliability for a joint structure joined with an adhesive cannot be ensured. In the field of aircraft in which the assurance of reliability is important, a joint structure made only with an adhesive is not allowed to be used in a structure. Accordingly, in a joint structure used in an aircraft, structure materials should be bonded to each other through fastener members.

BRIEF SUMMARY OF THE INVENTION

The present invention has been made in this background, and it is an object to provide a method of evaluating the joint state of a joint portion through kissing bond inspection using a non-destructive technique.

To solve this problem, a joint evaluation method according to the present invention uses the following solutions.

The present invention provides a joint evaluation method of evaluating a joint state of a joint portion in a composite including the joint portion in which an adherend and another adherend are joined to each other through an adhesive, the method including the steps of: applying an alternating-current signal to the joint portion; changing frequency to measure current and voltage; calculating an evaluation value related to a given electrical characteristic from a current value and a voltage value obtained by the measurement; comparing the evaluation value with a preset criterion related to the given electrical characteristic; and evaluating the joint state of the joint portion according to the amount of deviation of the evaluation value from the criterion.

In one aspect of the invention, the given electrical characteristic can be a dielectric constant, polarizability, capacitance, alternating-current resistance, or phase difference.

The present inventors have found after earnest research that the joint state of a joint portion can be evaluated by detection of a kissing bond, using an electrical technique. The joint state of a joint portion (the chemical state of a bonding interface) is reflected to an evaluation value related to given electrical characteristic obtained by changing the frequency. According to this invention, whether the chemical state of the bonding interface is in a normal state can be evaluated by comparing the evaluation value with a criterion (normal value) related to a given electrical characteristic. According to this invention, it can be evaluated that the smaller the amount of deviation of the evaluation value from the criterion, the closer the joint state of the joint portion to the normal state, and that the larger the amount of deviation, the weaker the chemical bonding at the bonding interface.

In one aspect of the invention, the current and the voltage may be measured while a given pressure is applied to a bonding interface in the joint portion. The pressure is greater than 1 kPa and less than or equal to 100 MPa.

Applying a pressure to the bonding interface changes the close contact state at the bonding interface. If current and voltage are measured in this state, the evaluation value related to a given electrical characteristic largely changes according to the chemical state at the bonding interface. Since the product may be damaged if the applied pressure is too high, the pressure is preferably less than or equal to 100 MPa.

In the case where a pressure is applied to the bonding interface, the current and the voltage are measured by bringing the electrodes into electrical contact with both ends of the bonding interface.

Bringing the electrodes into electrical contact with the bonding interface allows current to flow to the joint portion.

In one aspect of the invention, current and voltage may be measured by changing frequency without applying a given pressure to a bonding interface of the joint portion, a first evaluation value related to any one of dielectric constant, polarizability, and capacitance may be calculated from a current value and a voltage value obtained by the measurement, the first evaluation value may be compared with the criterion, and the joint state of the joint portion may be subjected to first evaluation according to the amount of deviation; current and voltage may be measured by changing frequency while a given pressure is applied to the bonding interface of the joint portion, a second evaluation value related to alternating-current resistance may be calculated from a current value and a voltage value obtained by the measurement, the second evaluation value may be compared with the criterion, and the joint state of the joint portion may be subjected to second evaluation according to the amount of deviation; and evaluation results of the first evaluation and the second evaluation may be correlated to give overall evaluation of the joint state of the joint portion.

Correlation of multiple evaluation results leads to accurate evaluation of the joint state.

According to the present invention, an electrical technique is used, so that the joint state of a joint portion can be evaluated by inspecting a kissing bond without destroying it.

DETAILED DESCRIPTION OF THE INVENTION

First Embodiment

Figure 1:
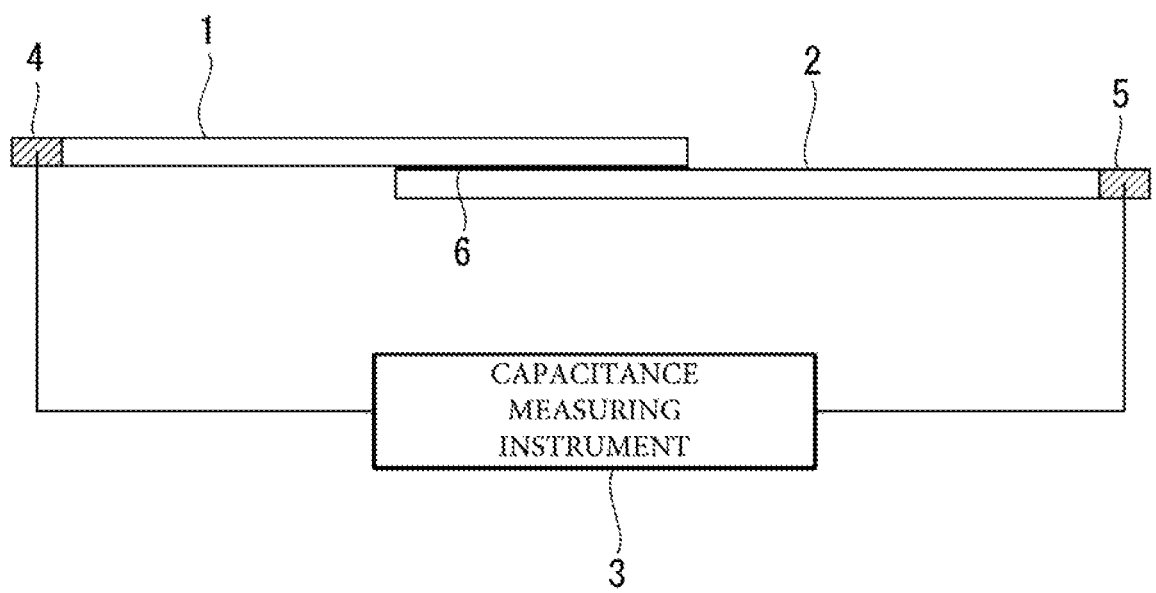
FIG. 1 is a schematic diagram of a measurement system used for a joint evaluation method according to a first embodiment.

An evaluation target to be evaluated by a joint evaluation method according to this embodiment will be first described. The evaluation target in this embodiment includes a joint portion in which an adherend and another adherend are bonded to each other through an adhesive.

The adherend and the other adherend are composed of different composites. A composite is composed of a bonding material (matrix) and microparticles or a fibrous material. The bonding material is, for example, an epoxy thermosetting resin or a PEEK thermoplastic resin. The microparticles are, for example, silica particles, carbon black, or fullerenes. The fibrous material is, for example, carbon fibers, glass fibers, or aramid fibers. Examples of a composite include, carbon fiber reinforced plastics (CFRPs), glass fiber reinforced plastics (GFRPs), and carbon fiber reinforced plastics (CFRTPs).

The adhesive is an epoxy adhesive, an acrylic adhesive, or a polyurethane adhesive. The thickness of the adhesive in the joint portion after curing is about 0.2 to 1 mm. The joint portion includes a bonding interface at which the adherend and the other adherend are joined (bonded) to each other.

A joint evaluation method according to this embodiment involves applying an alternating-current signal to a joint portion (Step S1), measuring the current and voltage by changing the frequency (Step S2), calculating an evaluation value related to a given electrical characteristic from the current value and the voltage value obtained by the measurement (Step S3), comparing the evaluation value with a preset criterion related to a given electrical characteristic (Step S4), and evaluating the joint state of a joint portion according to the amount of deviation of the evaluation value from the criterion (Step S5).

An alternating-current signal is alternating current or alternating-current voltage. To apply alternating-current signals, an electrical constant measuring instrument (capacitance measuring instrument), such as an LCR meter and an impedance meter, or an alternating current source can be used.

The frequency is changed in the range of 1 kHz to 100 GHz, preferably in the range of 100 MHz to 10 GHz.

The given electrical characteristic is at least one preliminarily selected from the group consisting of a dielectric constant, polarizability, capacitance, alternating-current resistance (impedance), and phase difference.

A criterion is preliminarily set for the selected given electrical characteristic. The criterion is preliminarily set, for example, using composite test pieces satisfying conditions (e.g., materials, shapes, and types of adhesive for the adherend and the other adherend) according to an actual evaluation target. To be specific, multiple composites that include joint portions joined with an adhesive and have similar shapes are prepared. Each composite is applied with an alternating-current signal to determine an evaluation value related to a given electrical characteristic, and inspection for a kissing bond is then performed by a destructive technique. A criterion is set to the average of evaluation values at which no kissing bond is detected or evaluation values at which the detected kissing bond is in an allowable range. A kissing bond can be detected by a technique using laser or other testing involving destruction. An evaluation value at which no kissing bond is detected indicates that a kissing bond is less than or equal to a detection limit. A criterion once set can be used for evaluation of a composite under the same conditions.

The allowable range of kissing bond is a range satisfying the bonding strength of the joint portion that the product requires. In setting a criterion, it is preferable to check the bonding strength of a joint portion in a composite and correlate the bonding strength and the amount of kissing bond (the level of chemical joint state) to each other, thereby determining the range of amount of kissing bond that ensures a required strength. The determined amount of kissing bond is correlated to the evaluation value of a given electrical characteristic of a test piece. Accordingly, the strength of the joint portion can be evaluated from the amount of deviation of the evaluation value from the criterion. At this time, it is preferable to set multiple thresholds so that the joint strength can be evaluated in stages with the evaluation value. A bonding strength can be checked by a tensile test, for example.

An evaluation value related to a given electrical characteristic is calculated by a computation on the current value and the voltage value obtained by the measurement. The evaluation value may be calculated by a computation performed by a function of an instrument for measuring the current and the voltage.

The calculated evaluation value is compared with the criterion, thereby obtaining the amount of deviation of the evaluation value from the criterion for each frequency. The joint state of a joint portion is evaluated according to the amount of deviation. For example, if the amount of deviation from the criterion exceeds a predetermined value, the evaluation result is poor bonding. For example, even if the evaluation value deviates from the criterion value, the evaluation result is good bonding if the amount of deviation does not exceed a threshold at which required bonding strength can be ensured.

It should be noted that it is preferable that a composite the evaluation result for which is poor bonding be reinforced with fastener members or the like.

Example 1

FIG. 1 is a schematic diagram of a measurement system used for the joint evaluation method according to the first embodiment. In FIG. 1, two plate-like adherends 1 and 2 composed of composites are joined to each other with an adhesive. Suppose that the given electrical characteristic is capacitance. The capacitance is measured by a capacitance measuring instrument 3. Electrodes 4 and 5 in the capacitance measuring instrument 3 are connected to ends of the adherends 1 and 2 so that a joint portion 6 (both ends of the bonding interface) can be sandwiched therebetween.

With the capacitance measuring instrument 3, an alternating-current signal is applied to the joint portion 6 and the current value and the voltage value are measured by changing the frequency. The capacitance is calculated by computation performed in the capacitance measuring instrument on the basis of the current value and the voltage value obtained by the measurement. The calculated capacitance is determined to be an evaluation value and the evaluation value is compared with the criterion of the capacitance.

Figure 2:
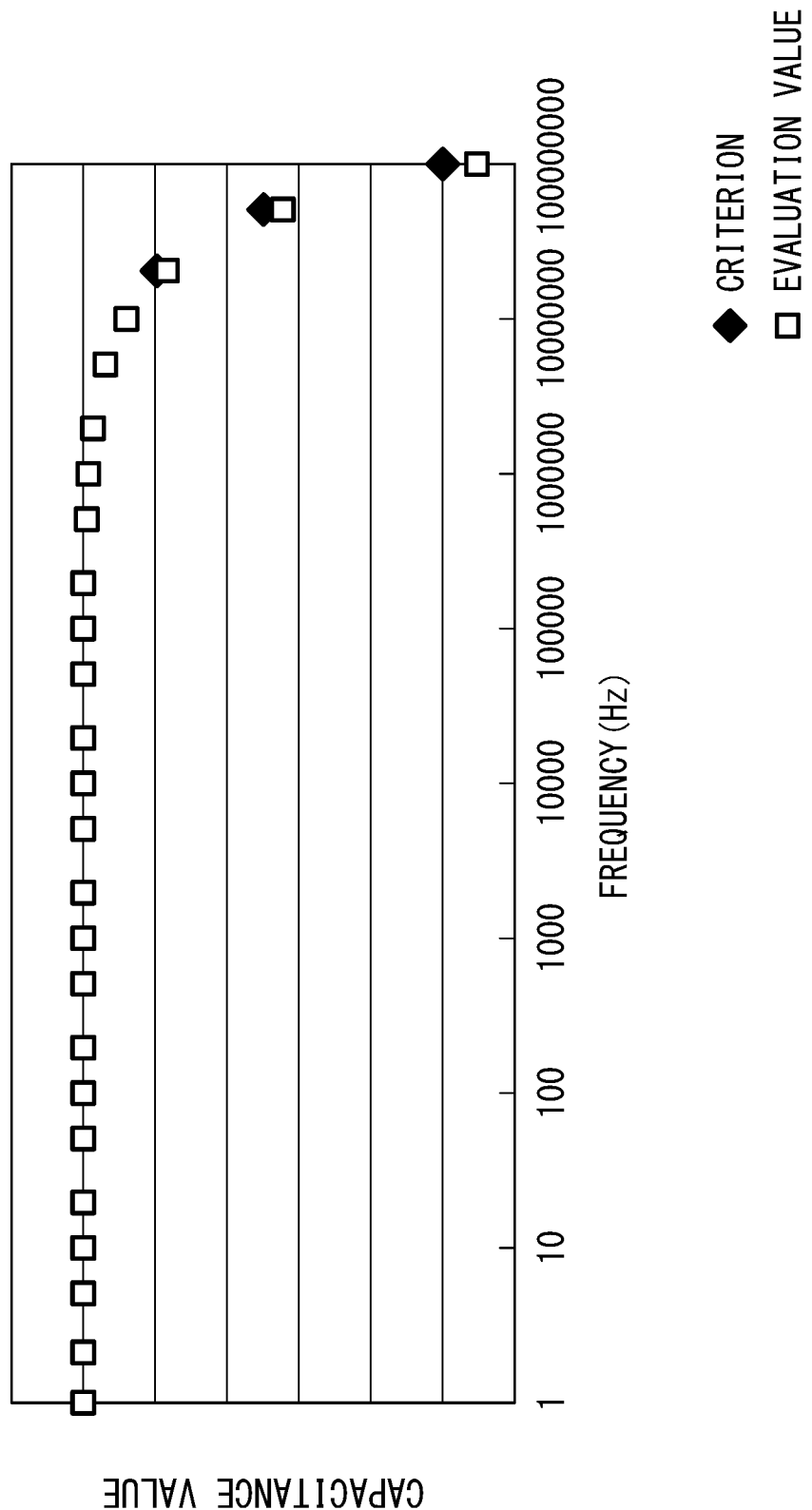
FIG. 2 is a graph showing comparisons of evaluation values with criteria.

FIG. 2 shows comparisons of evaluation values with criteria. In the drawing, the horizontal axis indicates frequency, and the vertical axis indicates capacitance values (specification values). Referring to FIG. 2, the capacitance values (evaluation values) at low frequencies barely deviate from the criteria (criteria values), while the evaluation values in a high frequency range (10 MHz to 100 MHz) deviate from the criteria. In FIG. 2, the amount of deviation is large at a high frequency, particularly 100 MHz. At 100 MHz in FIG. 2, the amount of deviation from the criterion, which is assumed to be 100, exceeds the threshold, so that the evaluation result is a poor joint state.

Example 2

Figure 3:
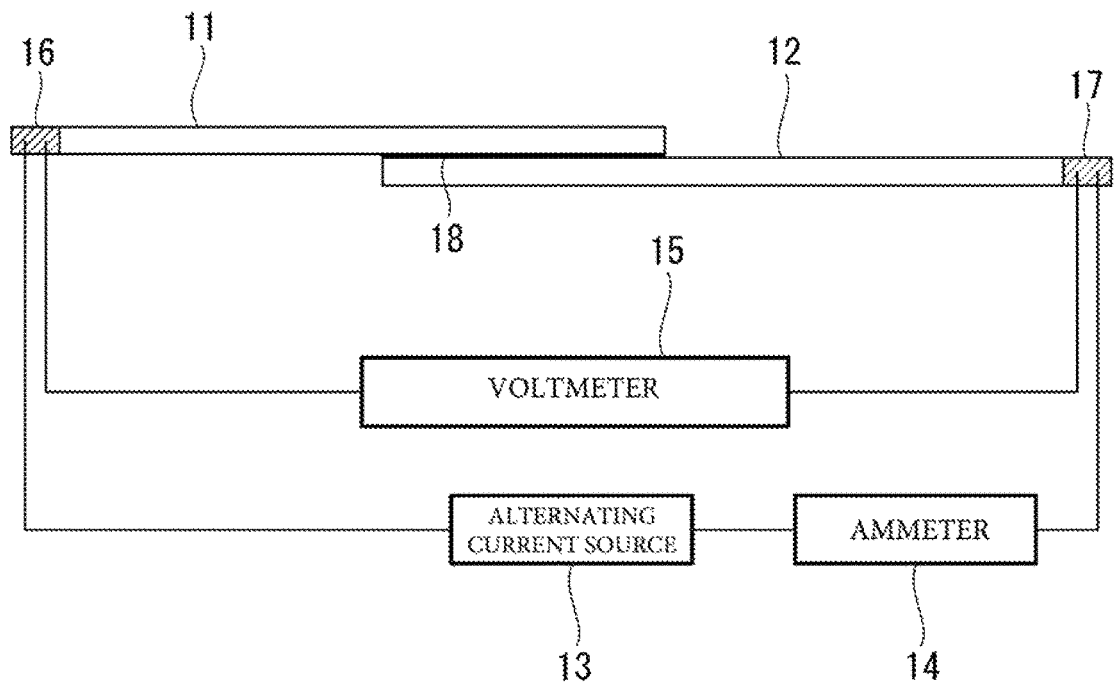
FIG. 3 is a schematic diagram of another measurement system used for the joint evaluation method according to the first embodiment.

FIG. 3 is a schematic view of another measurement system used for a joint evaluation method according to the first embodiment. In FIG. 3, two plate-like adherends 11 and 12 composed of composites are joined to each other with an adhesive. Suppose that the given electrical characteristic is alternating-current resistance. An alternating current source 13 is connected to an ammeter 14 in series. A voltmeter 15 and the ammeter 14 are disposed in parallel. Electrodes 16 and 17 of the voltmeter 15 and the ammeter 14 are connected to ends of the adherends 11 and 12 so that a joint portion 18 (both ends of the bonding interface) can be sandwiched therebetween.

An alternating-current signal is applied to the joint portion 18 by using the alternating current source 13. The current value and the voltage value are measured by changing the frequency. The alternating-current resistance (impedance=voltage/current) is calculated on the basis of the current value and the voltage value obtained by the measurement. The calculated alternating-current resistance is determined to be an evaluation value, the evaluation value is compared with the criterion of the alternating-current resistance, and the joint state is evaluated on the basis of the amount of deviation from the criterion.

Second Embodiment

This embodiment differs from the first embodiment in that it measures current and voltage while applying a given pressure to a joint portion. The description of the same configuration as in the first embodiment will be omitted.

For pressurization, a mechanical pressing device or a pressurization means, such as a Langevin type transducer, is used. With a pressurization means disposed adjacent to an adherend or another adherend, a given pressure toward the bonding interface is applied to the joint portion. The given pressure is greater than 1 kPa and less than or equal to 100 MPa. For the pressure, a constant pressure may be continuously applied or a sine-wave pressure may be periodically applied.

Like in the first embodiment, the given electrical characteristic is at least one preliminarily selected from the group consisting of a dielectric constant, polarizability, capacitance, alternating-current resistance (impedance), and phase difference. The given electrical characteristic is preferably an alternating-current resistance.

A criterion related to the selected given electrical characteristic is set. The criterion is set in the same manner as in the first embodiment after an evaluation value related to a given electrical characteristic is calculated by applying an alternating-current signal to a joint portion during application of a given pressure thereto.

An evaluation value related to a given electrical characteristic is calculated by a computation on the current value and the voltage value obtained by the measurement performed during pressurization of a joint portion.

The calculated evaluation value is compared with the criterion, thereby obtaining the amount of deviation of the evaluation value from the criterion for each frequency. Like in the first embodiment, the joint state of a joint portion is evaluated according to the amount of deviation.

According to this embodiment, the pressure applied to a joint portion is changed to dynamically change the bonding state of the joint portion so that a change between a normal state and a kissing bond state clearly appears, thereby increasing the evaluation accuracy.

Example 3

Figure 4:
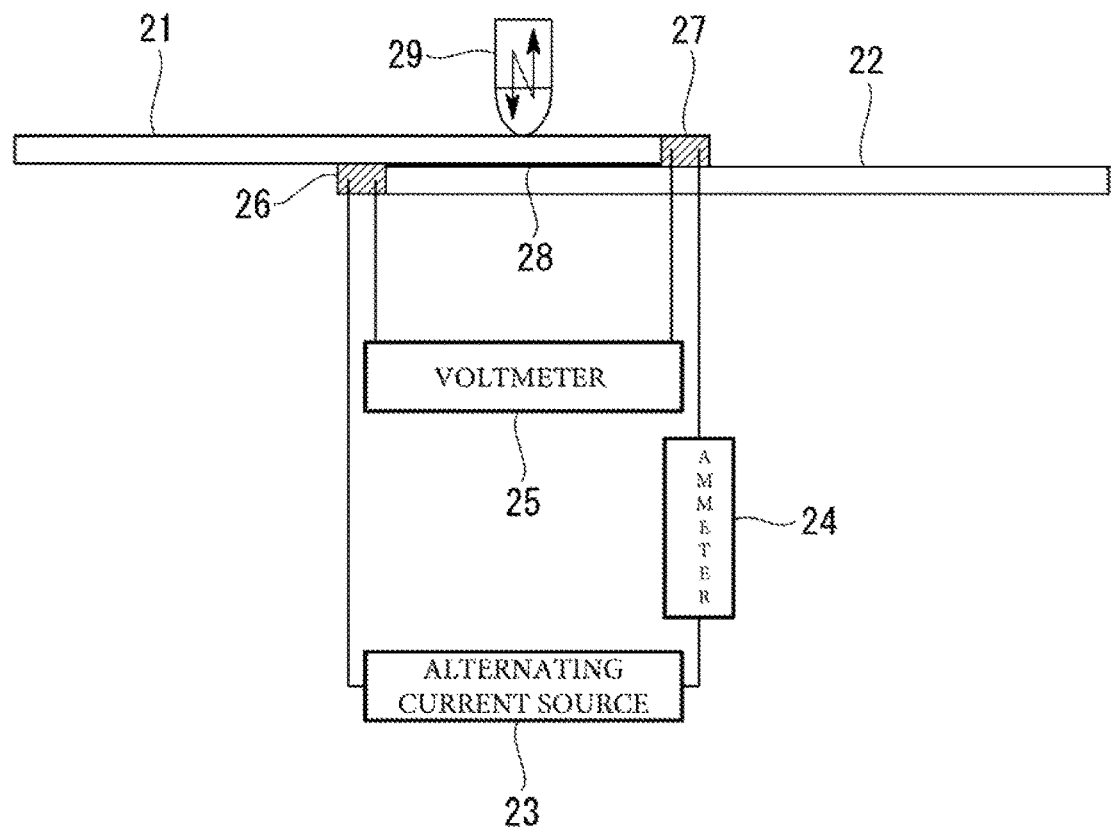
FIG. 4 is a schematic diagram of a measurement system used for a joint evaluation method according to a second embodiment.

FIG. 4 is a schematic diagram of a measurement system used for a joint evaluation method according to the second embodiment. In FIG. 4, two plate-like adherends 21 and 22 composed of composites are joined to each other with an adhesive. Suppose that the given electrical characteristic is alternating-current resistance. An alternating current source 23 is connected to an ammeter 24 in series. A voltmeter 25 and the ammeter 24 are disposed in parallel. Electrodes 26 and 27 of the voltmeter 25 and the ammeter 24 are connected to both ends of a joint portion 28 (bonding interface) such that they can be electrically connected to each other. A pressure probe 29 is disposed on the joint portion.

With a given pressure applied to the joint portion 28 through the pressure probe 29, an alternating-current signal is applied to the joint portion 28 using the alternating current source 23. The current value and the voltage value are measured by changing the frequency. The alternating-current resistance (impedance=voltage/current) is calculated on the basis of the current value and the voltage value obtained by the measurement. The calculated alternating-current resistance is determined to be an evaluation value, the evaluation value is compared with the criterion of the alternating-current resistance, and the amount of deviation of the evaluation value from the criterion is obtained for each frequency. Like in the first embodiment, the joint state of the joint portion 28 is evaluated according to the amount of deviation.

Example 4

Figure 5:
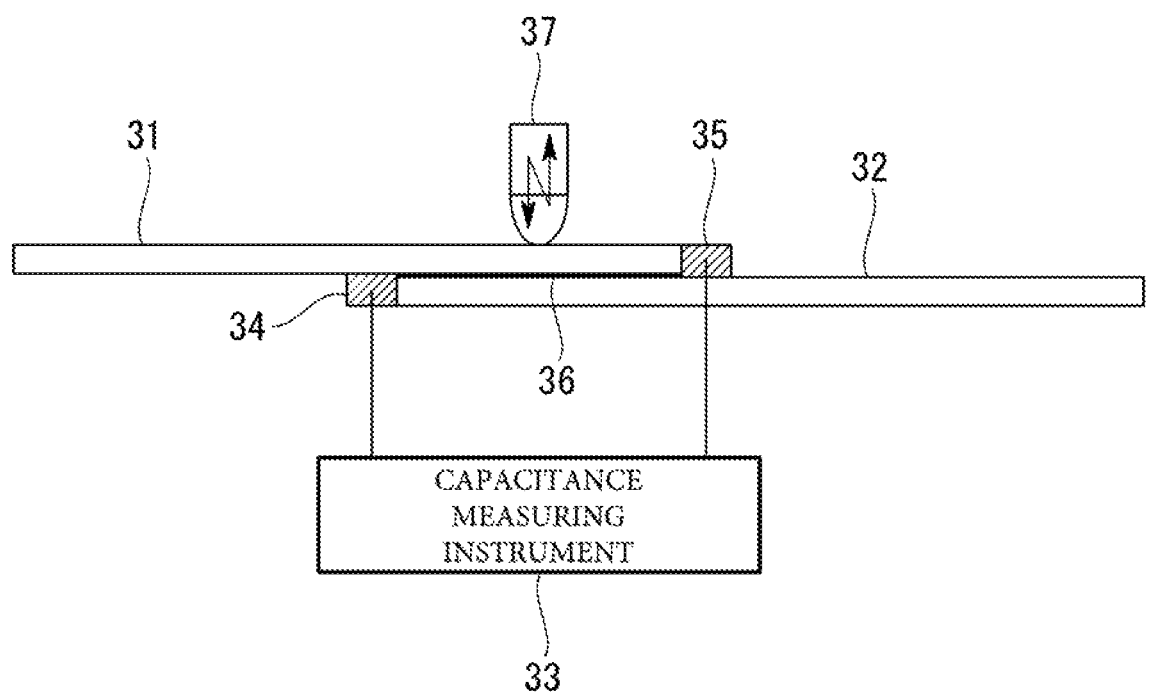
FIG. 5 is a schematic diagram of another measurement system used for the joint evaluation method according to the second embodiment.

FIG. 5 is a schematic view of another measurement system used for a joint evaluation method according to the second embodiment. In FIG. 5, two plate-like adherends 31 and 32 composed of composites are joined to each other with an adhesive. Suppose that the given electrical characteristic is capacitance. The capacitance is measured by a capacitance measuring instrument 33. Electrodes 34 and 35 of the capacitance measuring instrument 33 are connected to both ends of a joint portion 36 (bonding interface) such that they can be electrically connected to each other. A pressure probe 37 is disposed on the joint portion.

With a given pressure applied to the joint portion 36 through the pressure probe 37, an alternating-current signal is applied to the joint portion 36 and the current value and the voltage value are measured by changing the frequency with the capacitance measuring instrument 33. The capacitance is calculated by computation performed in the capacitance measuring instrument on the basis of the current value and the voltage value obtained by the measurement. The calculated capacitance is determined to be an evaluation value, the evaluation value is compared with the criterion of the capacitance, and the amount of deviation of the evaluation value from the criterion is obtained for each frequency. Like in the first embodiment, the joint state of the joint portion 28 is evaluated according to the amount of deviation.

Third Embodiment

In this embodiment, the joint state of a joint portion is subjected to first evaluation in accordance with the first embodiment. In addition, the joint state of the joint portion is subjected to second evaluation in accordance with the second embodiment. Overall evaluation of the joint state is performed by correlation of the first evaluation and the second evaluation. For the second evaluation, an electrical characteristic different from a given electrical characteristic selected for the first evaluation is selected.

First Evaluation

The given electrical characteristic is at least one selected from the group consisting of a dielectric constant, polarizability, and capacitance. An evaluation value is calculated and a joint state is subjected to first evaluation according to the first embodiment.

Second Evaluation

Suppose that the given electrical characteristic is alternating-current resistance. An evaluation value is calculated and the joint state is subjected to second evaluation according to the second embodiment.

The first evaluation and the second evaluation are correlated for overall evaluation of the joint state of the joint portion. For example, the amount of deviation determined by the first evaluation and the amount of deviation determined by the second evaluation are correlated and are compared with each other for overall evaluation. Correlation of the amounts of deviation determined in each evaluation allows the following evaluation, for example. In the first evaluation, multiple thresholds of the amount of deviation of evaluation value, which are denoted as $threshold_1$, $threshold_2$, $threshold_3$, and $threshold_4$, . . . are set. In the second evaluation, multiple thresholds are set in the same manner. If the amounts of deviation determined in each evaluation do not exceed the $threshold_1$, the evaluation result is a good joint state. If the amount of deviation determined in the first evaluation is between the $threshold_3$ and the $threshold_4$, but the amount of deviation determined in the second evaluation does not exceed the $threshold_2$, the evaluation result is a good joint state. Meanwhile, if the amount of deviation determined in the first evaluation is between the $threshold_3$ and the $threshold_4$, but the amount of deviation determined in the second evaluation is very close to the $threshold_4$, the evaluation result is a poor joint state. The joint state of a joint portion can be accurately evaluated by setting multiple thresholds for each evaluation so that the amounts of deviation can be correlated for evaluation.

REFERENCE SIGNS LIST 1, 11, 21, 31 adherend
2, 12, 22, 32 (another) adherend
3, 33 capacitance measuring instrument
4, 5, 16, 17, 26, 27, 34, 35 electrode
6, 18, 28, 36 joint portion
13, 23 alternating current source
14, 24 ammeter
15, 25 voltmeter
29, 37 pressure probe

The invention claimed is:

1. A joint evaluation method of evaluating a joint state of a joint portion in a composite including the joint portion in which a first adherend and a second adherend are joined to each other through an adhesive, the joint evaluation method comprising:
applying an alternating-current electrical signal to the joint portion;
changing frequency of the alternating-current electrical signal in a range of 100 MHz to 10 GHz to measure current and voltage;
calculating an evaluation value related to a given electrical characteristic from a current value and a voltage value obtained by the measurement;
comparing the evaluation value with a preset criterion related to the given electrical characteristic; and
evaluating the joint state of the joint portion according to an amount of deviation of the evaluation value from the preset criterion.

2. The joint evaluation method according to claim 1, wherein the given electrical characteristic is a dielectric constant, polarizability, capacitance, alternating-current resistance, or phase difference.

3. The joint evaluation method according to claim 1, wherein the current and the voltage are measured while a given pressure is applied to a bonding interface in the joint portion.

4. The joint evaluation method according to claim 3, wherein the given pressure is greater than 1 kPa and less than or equal to 100 MPa.

5. The joint evaluation method according to claim 3, wherein the current and the voltage are measured by bringing electrodes into electrical contact with both ends of the bonding interface.

6. A joint evaluation method of evaluating a joint state of a joint portion in a composite including the joint portion in which a first adherend and a second adherend are joined to each other through an adhesive, the joint evaluation method comprising:
applying an alternating-current electrical signal to the joint portion;
changing frequency of the alternating-current electrical signal in a range of 100 MHz to 10 GHz to firstly measure current and voltage without applying a given pressure to a bonding interface of the joint portion, calculating a first evaluation value related to any one of a dielectric constant, polarizability, and capacitance from a first current value and a first voltage value obtained by the first measurement, comparing the first evaluation value with a first preset criterion related to the one of the dielectric constant, polarizability, and capacitance, and subjecting the joint state of the joint portion is to a first evaluation according to a first amount of deviation of the first evaluation value from the first preset criterion;
changing frequency of the alternating-current electrical signal in the range of 100 MHz to 10 GHz to secondly measure current and voltage while the given pressure is applied to the bonding interface of the joint portion, calculating a second evaluation value related to alternating-current resistance from a second current value and a second voltage value obtained by the second measurement, comparing the second evaluation value with a second preset criterion related to the alternating-current resistance, and subjecting the joint state of the joint portion is to a second evaluation according to a second amount of deviation of the second evaluation value from the second preset criterion; and correlating evaluation results of the first evaluation and the second evaluation to give an overall evaluation of the joint state of the joint portion.

\* \* \* \* \*